United States Patent
Conrad et al.

(10) Patent No.: US 12,011,440 B2
(45) Date of Patent: Jun. 18, 2024

(54) READY-TO-ADMINISTER HYDROMORPHONE FORMULATIONS

(71) Applicant: Hikma Pharmaceuticals USA Inc., Eatontown, NJ (US)

(72) Inventors: Andrew Conrad, Bedford, OH (US); Bernadette Colvard, Bedford, OH (US)

(73) Assignee: Hikma Pharmaceuticals USA Inc., Eatontown, NJ (US)

( * ) Notice: Subject to any disclaimer, the term of this patent is extended or adjusted under 35 U.S.C. 154(b) by 0 days.

(21) Appl. No.: 17/656,149

(22) Filed: Mar. 23, 2022

(65) Prior Publication Data

US 2023/0301986 A1 Sep. 28, 2023

(51) Int. Cl.
*A61K 31/485* (2006.01)
*A61K 9/00* (2006.01)
*A61K 47/02* (2006.01)

(52) U.S. Cl.
CPC .......... *A61K 31/485* (2013.01); *A61K 9/0019* (2013.01); *A61K 47/02* (2013.01)

(58) Field of Classification Search
CPC .................................................. A61K 31/485
See application file for complete search history.

(56) References Cited

U.S. PATENT DOCUMENTS

| | | |
|---|---|---|
| 9,155,734 B2 | 10/2015 | Foster et al. |
| 11,207,309 B2 | 12/2021 | Conrad et al. |
| 11,213,480 B1 | 1/2022 | McAnany et al. |
| 11,471,400 B2 | 10/2022 | McAnany et al. |
| 11,738,011 B2 | 8/2023 | Conrad et al. |
| 2014/0262883 A1 | 9/2014 | Devouassoux et al. |
| 2023/0014425 A1 | 1/2023 | McAnany et al. |

FOREIGN PATENT DOCUMENTS

| | | | |
|---|---|---|---|
| WO | WO-2005020906 A2 * | 3/2005 | ........... A61K 31/485 |
| WO | 2014137385 A1 | 9/2014 | |
| WO | 2014140097 A1 | 9/2014 | |

OTHER PUBLICATIONS

Purdue Pharma L.P. drug label for Dilaudid® and Dilaudid-HP® Injection (Revised Jun. 2008) (Year: 2008).*
J. Huang 21, Drug Development & Delivery 28-31 (2021) (Year: 2021).*
Hikma Pharmaceuticals USA Inc. "Hydromorphone Hydrochloride—hydromorphone hydrochloride injection" 1-28 https://dailymed.nlm.nih.gov/dailymed/drugInfo.cfm?setid=67e79859-4efc-4ea7-8211-cadf746bc864 (Apr. 2020) (4 pages).
International Search Report and Written Opinion for International Patent Application No. PCT/US2022/071430, dated Jun. 8, 2022, 8 pages.
Anderson, C., et al., Pharmacy, 3, 379-385 (2015).
Ensom, H.H., et al., Can J Hosp Pharm, 62(2), 112-118 (2009).
Khondkar, D., et al., Int J Pharm Compounding, 14(2), 160-164 (2010).
Perks, Can J Hosp Pharm, 70(1), 74 (2017).
Walker, S.E., et al., Can J Hosp Pharm, 54, 193-201 (2001).
Co-pending U.S. Appl. No. 18/152,303, filed Jan. 10, 2023.

* cited by examiner

*Primary Examiner* — Nizal S Chandrakumar
(74) *Attorney, Agent, or Firm* — Neal, Gerber & Eisenberg LLP

(57) ABSTRACT

The present disclosure relates to a ready-to-administer (RTA), intravenous (IV) bag presentation for hydromorphone. In particular, the present disclosure relates to terminally sterilized liquid formulations comprising hydromorphone hydrochloride in sodium chloride packaged in an RTA IV bag. The present disclosure also relates to methods of treating patients by administration of such formulations and RTA IV bags containing such formulations.

18 Claims, 1 Drawing Sheet

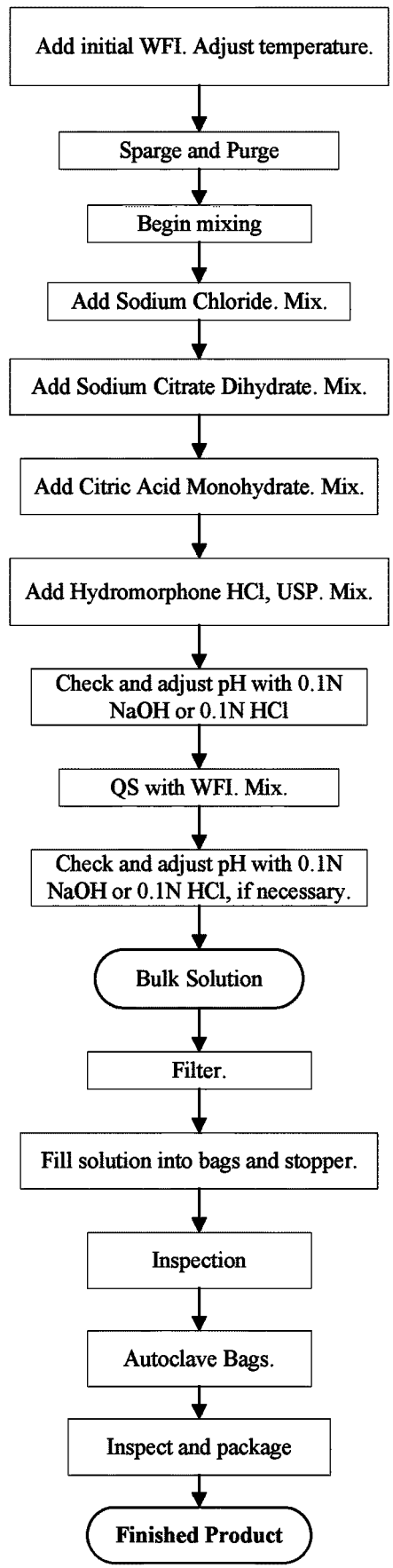

READY-TO-ADMINISTER HYDROMORPHONE FORMULATIONS

TECHNICAL FIELD

The present invention relates to ready-to-administer parenteral liquid formulations comprising hydromorphone or a pharmaceutically acceptable salt thereof, methods for preparing such formulations, methods for using such formulations, and polymeric infusion container filled with such formulations.

BACKGROUND

Hydromorphone is a semisynthetic phenanthrene alkaloid of opium; it is classified pharmacologically as a narcotic analgesic. Hydromorphone is indicated for the management of pain severe enough to require an opioid analgesic and for which alternate treatments are inadequate. Hydromorphone is typically used in the hydrochloride salt form.

Current hydromorphone hydrochloride products include an aseptically filled liquid product packaged in glass vials. The vial product is formulated at 2 mg/mL and marketed in 1 mL and 20 mL fills. Additional hydromorphone hydrochloride products include 1 mL single-dose prefilled syringes containing 0.2 mg/mL, 1 mg/mL, or 2 mg/mL hydromorphone hydrochloride.

Opioids such as hydromorphone are not available in volumes larger than what is currently provided by the approved formulations. To meet the need of patients that require longer term pain management and/or lower concentrations than commercially available, hospital and health system pharmacies have to prepare larger volumes of hydromorphone. Compounding larger volumes of hydromorphone to fill this gap of availability raises several concerns.

For example, dilution of commercially available hydromorphone hydrochloride products can introduce the potential for error in mixing and measuring diluents or other components. Dilution of commercially available products also suffers from the disadvantage of time-consuming dilution steps that introduce potential undesirable impurities with the use of external components.

Moreover, the stability of commercially available solutions, once diluted, is limited and not intended for long term storage. Perks et al. evaluated the stability of compounded 0.2 mg/mL hydromorphone hydrochloride in 0.9% sodium chloride stored in Continuous Ambulatory Delivery Device (CADD) reservoirs, PVC bags, and PAB® bags at room temperature. Can J Hosp Pharm, 70(1), 74 (2017). Over a 90 day period, water loss was apparent in PVC bags and CADD reservoirs, increasing concentrations by 8% and 6%, respectively. When corrected for water loss, the hydromorphone solution retained more than 97% of the initial concentration. Hydromorphone concentrations were not reported beyond 90 days nor were impurity levels or sterility reported by Perks; in fact, Perks does not specify any steps to maintain sterility of its compounded solution nor any impact of such steps on stability or impurity levels.

Khondkar et al. prepared a 0.2 mg/mL hydromorphone hydrochloride in 0.9% sodium chloride solution by diluting a commercially available hydromorphone hydrocholoride injectable solution and studied the stability and sterility of the solutions after storage for 16 and 34 weeks in PCA (Patient Controlled Analgesia) Injectors at 5° C. in refrigerator, 20° C. on benchtop, 20° C. in dark, 35° C. in dark, and 50° C. in dark. Int J Pharm Compd., 14(2), 160-164 (2010). The undiluted 2 mg/mL control in the original injectable vial (as it was supplied from the manufacturer), kept in the dark and at room temperature, demonstrated hydromorphone concentration of 100% from 1 to 8 weeks and 99.8% at 16 weeks. On the other hand, the percent of initial hydromorphone concentration remaining in the diluted solution in the PCA injectors decreased over time. At 16 weeks (112 days), the concentration of hydromorphone in the PCA injectors had decreased to 92% to 96% and by 34 weeks (238 days), the concentration of hydromorphone in the PCA injectors had decreased to 86% to 88% of the original value.

Anderson and MacKay determined the stability of 0.1 mg/mL hydromorphone hydrochloride in 0.9% sodium chloride compounded from hydromorphone 2 mg/mL and stored at room temperature in polypropylene syringes. Pharmacy, 3, 379-385 (2015). The 0.1 mg/mL hydromorphone hydrochloride in 0.9% sodium chloride was found to have only 90.3% of its original concentration remaining at 100 days. Anderson and MacKay acknowledged that at least some hydromorphone samples stored for 100 days would be designated as unstable and that their results do not imply sterility for the storage durations.

Finally, dilution of commercially available products increases the risk for contamination and may compromise sterility. Certain pharmaceutical solutions can be sterilized by heat treatment. However, it is known that for formulations containing heat-sensitive active ingredients like hydromorphone, heat treatment is counterproductive because it leads to an unacceptable increase in degradation products brought on by the excessive use of heat in the sterilization process. Indeed, WO2014/137385 ("Foster") demonstrated that heat-labile hydromorphone undergoes transformations to undesirable degradation products, particularly 2,2'-bishydromorphone (commonly known as pseudo-hydromorphone, PHM) during the terminal sterilization process. Foster demonstrated that the level of known impurities (and in particular PHM), unknown impurities at 0.80 relative retention time (RRT), and total impurities for its terminally sterilized solutions A-E were higher at each day tested as compared to a non-terminally sterilized control, demonstrating that terminal sterilization of its hydromorphone hydrochloride solutions adversely impacted stability of the solutions. Foster instead proposes aseptic processing as an alternative to terminal sterilization.

Thus, there remains a need for ready-to-administer injectable formulations of hydromorphone that offer long-term storage stability and can be terminally sterilized after filling.

SUMMARY OF THE INVENTION

This disclosure is directed to ready-to-administer parenteral liquid formulations comprising hydromorphone or a pharmaceutically acceptable salt thereof such as hydromorphone hydrochloride. These ready-to-administer formulations have been terminally sterilized in a polymeric infusion container and are stable upon long-term storage. As disclosed herein, terminally sterilized hydromorphone hydrochloride liquid formulations in polymeric infusion containers are stable upon long-term storage at room temperature such as from about 20° C. to about 25° C.

In one aspect, this disclosure provides a terminally sterilized hydromorphone hydrochloride in 0.9% sodium chloride packaged in a ready-to-administer (RTA) intravenous (IV) bag. In certain embodiments, the concentration of hydromorphone hydrochloride is 0.2 mg/mL, such as 10 mg in 50 mL packaged in a 50 mL RTA IV bag or 20 mg in 100 mL packaged in a 100 mL RTA IV bag.

This disclosure provides a ready-to-administer parenteral liquid formulation comprising hydromorphone hydrochloride; a tonicity adjusting agent; and a buffer system; wherein the liquid formulation has a pH of 3.5 to 4.5, wherein the liquid formulation has been terminally sterilized in a polymeric infusion container, and wherein the liquid formulation is stable for at least 6 months when stored at 25° C.±2° C. and not more than 40% RH.

This disclosure provides a ready-to-administer parenteral liquid formulation comprising 0.2 mg/mL of hydromorphone hydrochloride; 9 mg/mL of sodium chloride; 0.23 mg/mL of sodium citrate dihydrate; and 0.22 mg/mL of citric acid monohydrate; wherein the liquid formulation has a pH of 3.5 to 4.2, wherein the liquid formulation has been terminally sterilized in a polymeric infusion container, and wherein the liquid formulation is stable for at least 6 months when stored at 25° C.±2° C. and not more than 40% RH.

This disclosure also provides methods for making the ready-to-administer parenteral liquid formulations described herein. The methods comprise preparing a bulk solution comprising hydromorphone hydrochloride, filling the bulk solution into a polymeric infusion container, and terminally sterilizing the bulk solution in the polymeric infusion container.

The disclosure also provides methods for the management of pain using the ready-to-administer parenteral liquid formulations described herein. The methods comprise parenterally administering to a subject in need of management of pain the ready-to-administer parenteral liquid formulations described herein.

The disclosure also provides polymeric infusion containers filled with the ready-to-administer parenteral liquid formulations described herein. The polymeric infusion containers and their contents have been terminally sterilized.

These and other objects of the invention are described in the following paragraphs. These objects should not be deemed to narrow the scope of the invention.

BRIEF DESCRIPTION OF THE DRAWINGS

FIG. 1 is a process flow diagram for the manufacture of a terminally sterilized hydromorphone hydrochloride liquid formulation in a ready-to-administer bag.

DETAILED DESCRIPTION OF THE INVENTION

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. Definitions

As used in the specification and the appended claims, unless specified to the contrary, the following terms have the meaning indicated:

The term "about" refers generally to a range of numerical values (e.g., ±5 to 10% of the recited value) that one of ordinary skill in the art would consider equivalent to the recited value. Ranges can be expressed herein as from "about" one particular value, and/or to "about" another particular value. When such a range is expressed, the range is inclusive of the recited values.

The term "initial" when used in connection with a given parameter such as osmolality, pH, hydromorphone hydrochloride content, or impurities refers to that parameter at the time the hydromorphone hydrochloride composition is filled into the polymeric infusion container, prior to subjecting the polymeric infusion container and hydromorphone hydrochloride composition to terminal sterilization.

The term "pharmaceutically acceptable" is used adjectivally to mean that the modified noun is appropriate for use as a pharmaceutical product for human use or as a part of a pharmaceutical product for human use.

The term "subject" includes humans and other primates as well as other mammals. The term subject includes, for example, a patient, such as a cancer patient or a post-operative patient, suffering from or believed to be suffering from moderate to severe pain. In certain embodiments, the subject is a human.

The terms "treat", "treating" and "treatment" refer to a method of alleviating or abrogating a condition, disorder, or disease and/or the attendant symptoms thereof.

B. Drug Substance

Liquid formulations disclosed herein comprise at least one active pharmaceutical ingredient: hydromorphone or a pharmaceutically acceptable salt thereof. In one particular embodiment, the pharmaceutically acceptable salt of hydromorphone is hydromorphone hydrochloride.

Hydromorphone hydrochloride is chemically identified as 4,5α-epoxy-3-hydroxy-17-methylmorphinan-6-one hydrochloride. The molecular weight of hydromorphone hydrochloride is 321.80 and its molecular formula is $C_{17}H_{19}NO_3 \cdot HCl$. Hydromorphone hydrochloride has the following chemical structure:

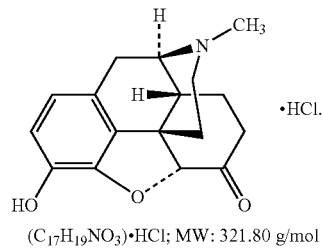

$(C_{17}H_{19}NO_3) \cdot HCl$; MW: 321.80 g/mol

Methods for synthesizing hydromorphone and a pharmaceutically acceptable salts thereof are known in the art and described, for example, in U.S. Pat. No. 6,589,960, the contents of which are herein incorporated by reference.

Other suitable hydromorphone salts include any water soluble salt of hydromorphone such as hydromorphone sulfate.

In certain embodiments, hydromorphone hydrochloride is present in the liquid formulation in an amount from about 0.01 mg/mL to about 2.0 mg/mL, alternatively from about 0.05 mg/mL to about 1.0 mg/mL, or alternatively from about 0.1 mg/mL to about 0.5 mg/mL. In some such embodiments, the liquid formulation comprises 0.2 mg/mL of hydromorphone hydrochloride.

C. Liquid Formulations

This disclosure provides a liquid formulation that is suitable for terminal sterilization in a polymeric infusion container and is stable upon long-term storage following such terminal sterilization. The liquid formulation may contain one or more excipients such as a tonicity adjusting agent, a pH adjusting agent, and/or a buffer system.

In certain embodiments, the disclosed liquid formulation comprises a tonicity adjusting agent.

In certain embodiments, the liquid formulation is isotonic or slightly hypotonic. In some such embodiments, the liquid formulation is isotonic.

In certain embodiments, the liquid formulation has an osmolality in the range from about 250 mOsmol/kg to about 375 mOsmol/kg, alternatively, about from about 270 mOsmol/kg to about 330 mOsmol/kg, or, alternatively, from about 285 mOsmol/kg to about 310 mOsmol/kg. In an exemplary embodiment, the osmolality of the liquid formulation is about 289 mOsmol/kg.

In certain embodiments, the osmolality of the liquid formulation is adjusted by addition of a tonicity adjusting agent. The tonicity adjusting agent that may be, without limitation, sodium chloride, calcium chloride, mannitol, glycerol, sorbitol, propylene glycol, dextrose, sucrose, and the like and mixtures thereof. In certain embodiments, the tonicity adjusting agent comprises sodium chloride, dextrose, and sucrose. In some such embodiments, the tonicity adjusting agent is sodium chloride.

In certain embodiments, the tonicity adjusting agent is sodium chloride. In some such embodiments, the liquid formulation comprises from about 0.5% w/v to about 1.2% w/v sodium chloride. In an exemplary embodiment, the liquid formulation comprises about 0.9% w/v sodium chloride.

In certain embodiments, the liquid formulation has an initial pH in the range of about 3.5 to about 4.5, alternatively from about 3.5 to about 4.2, alternatively from about 3.5 to 4.0, or alternatively from about 3.6 to about 3.8. In an exemplary embodiment, the liquid formulation has an initial pH in the range of about 3.5 to about 4.5. In another exemplary embodiment, the liquid formulation has an initial pH in the range of about 3.6 to about 3.8, preferably about 3.7.

In certain embodiments, the disclosed liquid formulation comprises a pH adjusting agent.

In certain embodiments, the pH of the liquid formulation is adjusted by addition of a pH adjusting agent. The pH adjusting agent that may be, without limitation, an acid such as sulfuric acid, phosphoric acid, or hydrochloric acid, a base such as sodium acetate, sodium bicarbonate, or sodium hydroxide, or a combination thereof.

In certain embodiments, the pH adjusting agent is hydrochloric acid, sodium hydroxide, or a combination thereof.

The concentration of the pH adjusting agent can be any concentration suitable for adjusting the pH, such as, for example, 0.1 N acid or base. In certain embodiments, 0.1 N hydrochloric acid and/or 0.1 N sodium hydroxide are added to obtain the desired pH.

In certain embodiments, the disclosed liquid formulation comprises a buffer system.

In certain embodiments, the pH of the liquid formulation is maintained within the preferred range by addition of a buffer system. The buffer system may be, without limitation, a phosphate buffer, a citrate buffer, an acetate buffer, a histidine buffer, or a combination thereof.

In certain embodiments, the buffer system comprises a citrate buffer. In some such embodiments, the liquid formulation comprises from about 0.1 mg/mL to about 1.0 mg/mL of the citrate buffer.

In certain embodiments, the buffer system comprises sodium citrate, citric acid, or a combination thereof. Examples of sodium citrate and citric acid include anhydrous forms as well as hydrates, such as sodium citrate dihydrate, trisodium citrate anhydrous, trisodium citrate dihydrate, trisodium citrate pentahydrate, citric acid anhydrous, and citric acid monohydrate.

In certain embodiments, the buffer system comprises sodium citrate dihydrate and citric acid monohydrate. In some such embodiments, the liquid formulation comprises from about 0.01% w/v to about 0.1% w/v sodium citrate dihydrate and from about 0.01% w/v to about 0.1% w/v citric acid monohydrate. In an exemplary embodiment, the liquid formulation comprises about 0.02% (w/v) of sodium citrate dihydrate and about 0.02% (w/v) of citric acid monohydrate.

In certain embodiments, the buffer system stabilizes the pH of the liquid formulation.

Thus, for example, a pH adjusting agent and/or a buffer system may be present in the liquid formulation in an amount sufficient to provide and maintain a pH of about 3.5 to about 4.5, alternatively, from about 3.5 to 4.0, or alternatively from about 3.6 to about 3.8.

In certain embodiments, the liquid formulation further comprises a chelating agent. Exemplary chelating agent include, but are not limited to, ethylenediaminetetraacetic acid (EDTA). However, in certain embodiments, the liquid formulation is substantially free of chelating agents.

Exemplary preservatives include, but are not limited to, methylparaben, propylparaben, or a combination thereof. However, in certain embodiments, the liquid formulation is substantially free of preservatives.

Thus, in certain embodiments, the liquid formulation optionally contains a chelating agent and/or a preservative. However, in certain other embodiments, the liquid formulation is substantially free of chelating agents and/or preservatives.

This disclosure provides a ready-to-administer parenteral liquid formulation comprising hydromorphone hydrochloride, a tonicity agent, a buffer system, one or more pH adjusting agents, and water for injection. An exemplary embodiment is provided in Table 1 below.

TABLE 1

| Ingredient | Function | Amount per mL |
|---|---|---|
| Hydromorphone Hydrochloride, USP | Active Ingredient | 0.2 mg |
| Sodium Chloride, USP | Tonicity | 9 mg |
| Sodium Citrate Dihydrate, USP | Buffering | 0.23 mg |
| Citric Acid Monohydrate, USP | Buffering | 0.22 mg |
| Sodium Hydroxide, NF | pH adjustment | pH adjustment |
| Hydrochloric Acid, NF | pH adjustment | pH adjustment |
| Water for Injection, USP | Aqueous Vehicle | q.s. ad 1 ml |

D. Polymeric Infusion Containers

The hydromorphone hydrochloride formulations disclosed herein are ideally ready-to-administer (RTA) formulations for parenteral administration without the need for reconstitution or further dilution. The ready-to-administer formulations are liquid stored in a pharmaceutically acceptable container, for example, an infusion container such as polymeric infusion container (e.g., intravenous (IV) bag). Diluents can include, for instance, fluids suitable for parenteral administration such as sodium chloride solutions.

Exemplary materials for the containers and container components include, but are not limited to, polyolefins, polysulfone, polycarbonate, polypropylene, polyethylene (such as low density polyethylene (LDPE) or high density polyethylene (HDPE)), polystyrene, and co-polymers thereof. Preferably, the materials for the container and container components are suitable to withstand aseptic filling and not deform during terminal sterilization. In certain embodiments, the polymeric infusion container comprises a polyolefin/styrene block copolymer, such as the polymeric IV bags manufactured by PolyCine.

The infusion container can be a flexible plastic container, optionally with ports and closure system for storing the liquid formulations. Infusion containers can include other conventional components, for example, connection ports, connector caps or connector disks.

The infusion containers may be sealed with any appropriate closure, such as a twist-off stopper. An exemplary twist-off stopper comprises a polypropylene film, such as Inerta® supplied by Technoflex®.

In certain embodiments, the hydromorphone hydrochloride liquid formulation is prepared as a 50 mL fill or a 100 mL fill packaged in a 50 mL or 100 mL, respectively, polymeric infusion container, such as a single port IV bag with a twist-off stopper.

An exemplary polymeric infusion container and closure system for hydromorphone hydrochloride is provided in Table 2 below.

TABLE 2

| Component | Description |
| --- | --- |
| IV Bag and Tube | Bag: 100 cc, PolyCine APP114 multilayer Polyolefin/Styrene block copolymer, 200 μm<br>Tube: APP 107, 1000 μm |
| Twist-off Stopper | Polypropylene twist-off, made with Inerta® 016 TP823 |

E. Terminal Sterilization

General procedures for filling the liquid formulation into the polymeric infusion containers and their subsequent processing, for example, terminal sterilization, are known in the art.

Processing techniques of the formulations filled in an infusion container preferably use a sterilization process to destroy or eliminate any microorganisms that may be present in the hydromorphone hydrochloride formulations following preparation. For example, terminal sterilization can be used to destroy or eliminate any microorganisms that may be present in the sealed polymeric infusion container containing the hydromorphone hydrochloride liquid formulation. An autoclave is commonly used to accomplish terminal heat-sterilization of drug products in their final packaging.

In certain embodiments, the polymeric infusion container filled with the liquid formulation containing hydromorphone hydrochloride is terminally sterilized using an autoclave, such as water cascade autoclave. The liquid formulations in the polymeric infusion containers can be autoclaved at a temperature ranging from 115° C. to 130° C., preferably at a temperature ranging from 119° C. to 122° C., for a period of time ranging from about 5 to about 30 minutes, alternatively from about 5 to about 15 minutes, alternatively from about 6 to about 11 minutes.

In certain embodiments, a terminal sterilization cycle is based on a $D_{121}$-value or decimal reduction time. In some such embodiments, the terminal sterilization cycle is based on a $D_{121}$-value that is less than 1.5, alternatively less than 1.0, such as about 0.5.

In certain embodiments, terminal sterilization can be characterized by specifying a $F_0$ value. The $F_0$ value is the equivalent time in minutes at the specified temperature that gives the same thermal lethality as at 121° C. For example, if a cycle has an $F_0$ value of 6, the sterilization effectiveness of that cycle is equal to 6 minutes at 121° C. regardless of the process temperature and time used in the cycle. In some such embodiments, the $F_0$ is less than 20, such as from about 5 to about 15, alternatively from about 6 to about 11. In some such embodiments, the $F_0$ is about 6. In some such embodiments, the $F_0$ is not more than about 15, alternatively not more than about 12, alternatively not more than about 11.

As described herein, it was observed that the hydromorphone hydrochloride liquid formulations contained in a polymeric infusion container can withstand terminal sterilization cycles up to $F_0$ of 15 minutes. Thus, in some such embodiments, the $F_0$ does not exceed 15.

In certain embodiments, the liquid formulation containing hydromorphone hydrochloride is substantially free of viable microbial contamination after terminal sterilization. Methods for assessing microbial contamination are known in the art and include testing for sterility in accordance with USP <71> using Trypticase Soy Broth (Soybean-Casein Digest Medium), which is suitable for the culture of both fungi and aerobic bacteria and/or Fluid Thioglycolate Medium, which is a medium primarily intended for the culture of anaerobic bacteria.

F. Compounding Procedure

In one aspect, this disclosure provides a method for manufacturing a terminally sterilized, 0.2 mg/mL presentation of hydromorphone hydrochloride in 0.9% sodium chloride packaged in a polymeric infusion container such as an RTA IV bag.

In certain embodiments, compounding takes place in a controlled environment in a stainless steel vessel equipped with a mixer.

FIG. 1 depicts an exemplary process flow diagram for the manufacture of a terminally sterilized hydromorphone hydrochloride formulation packaged in an RTA IV bag.

At step 1, add 80% of the water for injection (WFI) to an empty compounding vessel.

At step 2, begin a nitrogen purge and sparge. Maintain both purge and sparge throughout formulation.

At step 3, begin mixing at an appropriate rpm.

At step 4, add calculated amount of Sodium Chloride to the compounding vessel (e.g., to achieve a final concentration of 9 mg/mL). Mix for at least 5 minutes. Verify dissolution of the Sodium Chloride.

At step 5, add calculated amount of Sodium Citrate Dihydrate to the compounding vessel (e.g., to achieve a final concentration of 0.23 mg/mL). Mix for at least 5 minutes. Verify dissolution of the Sodium Citrate Dihydrate.

At step 6, add calculated amount of Citric Acid Monohydrate to the compounding vessel (e.g., to achieve a final concentration of 0.22 mg/mL). Mix for at least 5 minutes. Verify dissolution of the Citric Acid Monohydrate.

At step 7, add calculated amount of hydromorphone hydrochloride, USP to the compounding vessel (e.g., to achieve a final concentration of 0.2 mg/mL). Mix for at least 5 minutes. Verify dissolution of the hydromorphone hydrochloride.

At step 8, measure pH and adjust to 3.6 to 3.8 (Target 3.7) using 0.1 N Sodium Hydroxide or 0.1 N Hydrochloric Acid solution. Mix for at least 5 minutes between each addition.

At step 9, add WFI to QS until final solution weight is reached and mix for at least 10 minutes and confirm the homogeneity of the solution.

At step 10, measure pH and adjust to 3.6 to 3.8 (Target 3.7) using 0.1 N Sodium Hydroxide or 0.1 N Hydrochloric Acid, if necessary. Mix for at least 5 minutes between each addition.

Subsequent filtration and filling may occur in a controlled environment.

At step 11, the bulk solution is pressure transferred from the holding vessel through PFA tubing and stainless steel contact parts and one 10 inch 0.22 μm Durapore cartridge filter housed in stainless steel.

At step 12, the filtered bulk solution is pressurized through the filling setup composed of PFA tubing and stainless steel contact parts, through a stainless steel filling needle and then filled into IV bags. Once filled, the bags will be stoppered with a twist-off stopper.

At step 13, the bags are inspected.

At step 14, filled bags are terminally sterilized using a water cascade autoclave at a temperature of 121° C. and a set $F_o$ of 6.0.

At step 15, autoclaved bags are dried, inspected, and placed in an aluminum overwrap pouch for storage.

G. Stability

Hydromorphone hydrochloride is heat and light sensitive and reactive with strong oxidizing agents. Degradation products of hydromorphone hydrochloride include dihydromorphine, hydromorphone N-oxide, and 2,2'-bishydromorphone.

In at least one aspect, the terminally sterilized liquid formulations disclosed herein are stable during, for example, storage, distribution, and the duration of the product's shelf-life (e.g., up to two years at room temperature/ambient conditions). A stable terminally sterilized liquid formulations may, for example, exhibit less degradation of the active ingredient and/or low amounts of degradation products. Assay and degradation product determination of liquid formulations may be performed using High Performance Liquid Chromatography ("HPLC") with UV detection In certain embodiments, the terminally sterilized hydromorphone hydrochloride liquid formulation packaged in a polymeric infusion container such as an IV bag meets release specifications and/or shelf-life specifications for hydromorphone hydrochloride, particular related substances, total related substances, and/or individual unknown impurities. In some such embodiments, the amount of hydromorphone hydrochloride, related substances, and/or individual unknown impurities is determined by HPLC.

Exemplary release specifications for hydromorphone hydrochloride are at least 93%, at least 94%, at least 95%, at least 96%, at least 97%, at least 98%, or at least 99% of the specified amount of hydromorphone hydrochloride (e.g., 0.2 mg/mL).

Exemplary release specifications for related compounds, such as dihydromorphine, hydromorphone N-oxide, 2,2'-bishydromorphone are not more than 0.75%, not more than 0.60%, not more than 0.45%, not more than 0.30%, or not more than 0.15% of the particular related compound.

Exemplary release specifications for total related compounds, which includes dihydromorphine, hydromorphone N-oxide, 2,2'-bishydromorphone as well as individual unknown impurities, are not more than 3.0%, not more than 2.0%, not more than 1.5%, not more than 1.25%, not more than 1.0%, not more than 0.75%, or not more than 0.5%.

Exemplary shelf-life specifications for hydromorphone hydrochloride are at least 90%, at least 91%, at least 92%, at least 93%, at least 94%, at least 95%, at least 96%, at least 97%, or at least 98% of the specified amount of hydromorphone hydrochloride (e.g., 0.2 mg/mL).

Exemplary shelf-life specifications for related compounds, such as dihydromorphine, hydromorphone N-oxide, 2,2'-bishydromorphone are not more than 1.0%, not more than 0.9%, not more than 0.8%, not more than 0.7%, not more than 0.6%, not more than 0.5%, not more than 0.4%, not more than 0.3%, not more than 0.2%, or not more than 0.1% of the particular related compound.

Exemplary shelf-life specifications for total related compounds, which includes dihydromorphine, hydromorphone N-oxide, 2,2'-bishydromorphone as well as individual unknown impurities, are not more than 3.0%, not more than 2.0%, not more than 1.5%, not more than 1.25%, not more than 1.0%, not more than 0.75%, or not more than 0.5%.

Stability of a terminally sterilized hydromorphone hydrochloride liquid formulation packaged in a polymeric infusion container such as an IV bag may be assessed following storage for at least two weeks, at least 1 month, at least 2 months, at least 3 months, at least 6 months, at least 12 months, at least 15 months, at least 18 months, or at least 24 months. In particular, pH, osmolality, hydromorphone concentration, degradation products or other impurities, may be assessed after storage for about 1, 2, 3, 6, 9, 12, 15, 18, 24, 36, and/or 48 months. Storage conditions may be long term, intermediate, or accelerated conditions. In particular, storage conditions may be, for example, 25° C.±2° C. and 40% relative humidity (RH)±5% RH, 30° C.±2° C. and 65% RH±5% RH, and/or 40° C.±2° C. and not more than 25% RH.

In certain embodiments, storage of the terminally sterilized hydromorphone hydrochloride liquid formulation packaged in a polymeric infusion container is at 25° C.±2° C. and 40%±5% relative humidity for between about 1 month and about 48 months, between about 2 months and about 36 months, or between about 3 months and about 24 months. In certain embodiments, storage of the terminally sterilized hydromorphone hydrochloride liquid formulation packaged in a polymeric infusion container is at 25° C.±2° C. and 40%±5% relative humidity for at least 3 months, at least 6 months, at least 12 months, at least 15 months, at least 18 months, or at least 24 months. In some such embodiments, storage stability is assessed at about 3, 6, 9, 12, 15, 18, 24, and/or 36 months.

In certain embodiments, storage of the terminally sterilized hydromorphone hydrochloride liquid formulation packaged in a polymeric infusion container is at 30° C.±2° C. and 65%±5% relative humidity for between about 1 month and about 24 months or between about 1 month and about 12 months. In certain embodiments, storage of the terminally sterilized hydromorphone hydrochloride liquid formulation packaged in a polymeric infusion container is at 30° C.±2° C. and 65%±5% relative humidity for at least 2 months, at least 3 months, at least 6 months, or at least 12 months. In some such embodiments, storage stability is assessed at about 1, 2, 3, 6, and/or 12 months.

In certain embodiments, storage of the terminally sterilized hydromorphone hydrochloride liquid formulation packaged in a polymeric infusion container is at 40° C.±2° C. and not more than 25% relative humidity for between about 1 month and about 12 months or between about 1 month and about 6 months. In certain embodiments, storage of the terminally sterilized hydromorphone hydrochloride liquid formulation packaged in a polymeric infusion container is at 40° C.±2° C. and not more than 25% relative humidity for at least 2 months, at least 3 months, or at least 6 months. In some such embodiments, storage stability is assessed at about 1, 2, 3, and/or 6 months.

Storage stability assessments may include pH, osmolality, hydromorphone concentration, degradation products or other impurities including but not limited to 2,2'-bi shydromorphone, dihydromorphine, and hydromorphone N-oxide.

In certain embodiments, the terminally sterilized hydromorphone hydrochloride liquid formulation packaged in a polymeric infusion container such as an IV bag has a pH in the range of about 3.5 to about 4.5, alternatively, from about 3.5 to 4.0, or alternatively from about 3.6 to about 4.0 after storage for up to 6 months, up to 9 months, up to 12 months, up to 15 months, up to 18 months, or up to 24 months under long-term stability conditions. In some such embodiments, the terminally sterilized hydromorphone hydrochloride liquid formulation packaged in a polymeric infusion container such as an IV bag has a pH of about 3.6, about 3.7, about 3.8, about 3.9, or about 4.0 after storage for up to 6 months, up to 9 months, up to 12 months, up to 15 months, up to 18 months, or up to 24 months under long-term stability conditions.

In certain embodiments, the pH of the terminally sterilized hydromorphone hydrochloride liquid formulation packaged in a polymeric infusion container such as an IV bag does not materially change over time under long-term stability conditions.

In certain embodiments, the terminally sterilized hydromorphone hydrochloride liquid formulation packaged in a polymeric infusion container such as an IV bag retains at least 90%, alternatively at least 91%, alternatively at least 92%, alternatively at least 93%, alternatively at least 94%, alternatively at least 95%, alternatively at least 96%, alternatively at least 97%, or alternatively at least 98% of the hydromorphone hydrochloride in the liquid formulation after storage for up to 6 months, up to 9 months, up to 12 months, up to 15 months, up to 18 months, or up to 24 months under long-term stability conditions as determined by HPLC.

In some such embodiments, the amount of hydromorphone hydrochloride retained following storage is with reference to the hydromorphone hydrochloride concentration prior to storage. In some such embodiments, the hydromorphone hydrochloride concentration prior to storage is from about 0.01 mg/mL to about 2.0 mg/mL, alternatively from about 0.05 mg/mL to about 1.0 mg/mL, or alternatively from about 0.1 mg/mL to about 0.5 mg/mL. In some such embodiments, the hydromorphone hydrochloride concentration prior to storage is 0.2 mg/mL. In some such embodiments, the amount of hydromorphone hydrochloride retained following storage is with reference to a product label claim. In some such embodiments, the product label claim for hydromorphone hydrochloride is from about 0.01 mg/mL to about 2.0 mg/mL, alternatively from about 0.05 mg/mL to about 1.0 mg/mL, or alternatively from about 0.1 mg/mL to about 0.5 mg/mL. In some such embodiments, the product label claim for hydromorphone hydrochloride is 0.2 mg/mL.

In certain embodiments, the amount of hydromorphone hydrochloride in the terminally sterilized hydromorphone hydrochloride liquid formulation packaged in a polymeric infusion container such as an IV bag does not materially change over time under long-term stability conditions.

In certain embodiments, the terminally sterilized hydromorphone hydrochloride liquid formulation packaged in a polymeric infusion container such as an IV bag contains not more than not more than 1.0%, not more than 0.9%, not more than 0.8%, not more than 0.7%, not more than 0.6%, not more than 0.5%, not more than 0.4%, not more than 0.3%, not more than 0.2%, or not more than 0.1% of any individual related substance (e.g., dihydromorphine, hydromorphone N-oxide, 2,2'-bishydromorphone) after storage for up to 6 months, up to 9 months, up to 12 months, up to 15 months, up to 18 months, or up to 24 months under long-term stability conditions as determined by HPLC.

In certain embodiments, the liquid formulation is stable for at least 12 months or at least 18 months when stored at 25° C.±2° C. and 40% relative humidity (RH)±5% RH. In some such embodiments, the liquid formulation is stable for up to 24 months when stored at 25° C.±2° C. and 40% relative humidity (RH)±5% RH.

In some such embodiments, the liquid formulation retains at least 90% w/w, preferably at least 95% w/w, and more preferably at least 98% of the hydromorphone hydrochloride and has not more than 10% w/w, preferably not more than 5% w/w, and more preferably not more than 2% w/w of total related substances after storage at 25° C.±2° C. and 40% RH±5% RH for 12, 18, or 24 months.

In some such embodiments, the liquid formulation retains at least 90% w/w, preferably at least 95% w/w, and more preferably at least 98% of the hydromorphone hydrochloride and has not more than 0.8% w/w, preferably not more than 0.5% w/w, and more preferably not more than 0.3% w/w of any individual related substance (e.g., dihydromorphine, hydromorphone N-oxide, 2,2'-bishydromorphone) after storage at 25° C.±2° C. and 40% RH±5% RH for 12, 18, or 24 months.

In some such embodiments, the pH of the liquid formulation after storage at 25° C.±2° C. and 40% RH±5% RH for 12, 18, or 24 months is in the range of about 3.5 to about 4.5, alternatively, from about 3.5 to 4.0, or alternatively from about 3.6 to about 4.0. In an exemplary embodiment, the pH of the liquid formulation after storage at 25° C.±2° C. and 40% RH±5% RH for 12, 18, or 24 months is in the range of about 3.6 to about 4.0, preferably about 3.6 to 3.8.

H. Methods of Use

In at least one aspect, this disclosure provides methods for the management of pain using the liquid formulations described herein. Liquid formulations comprising hydromorphone or a pharmaceutically acceptable salt thereof may be used for the management of pain and, in particular, for the management of pain severe enough to require an opioid analgesic and for which alternate treatments are inadequate. Liquid formulations described herein may preferably be parenterally administered to a subject in need thereof. In particular, liquid formulations described herein may be intravenously administered to a subject in need thereof.

Thus, in certain embodiments, the methods comprise parenterally administering to a subject in need of management of pain the terminally sterilized hydromorphone hydrochloride liquid formulations described herein. In some such embodiments, the methods comprise intravenously administering to a subject in need of management of pain the terminally sterilized hydromorphone hydrochloride liquid formulations described herein.

In certain embodiments, the subject is a human.

The liquid formulations, methods, and uses described herein will be better understood by reference to the following exemplary embodiments and examples, which are included as an illustration of and not a limitation upon the scope of the invention.

I. Exemplary Embodiments

Exemplary Embodiment 1. A ready-to-administer parenteral liquid formulation comprising (a) hydromorphone hydrochloride; (b) a tonicity adjusting agent; and (c) a buffer system; wherein the liquid formulation has a pH of 3.5 to 4.5, wherein the liquid formulation has been terminally sterilized in a polymeric infusion container, and wherein the liquid formulation is stable for at least 6 months when stored at 25° C.±2° C. and 40% relative humidity (RH)±5% RH.

Exemplary Embodiment 2. The liquid formulation of embodiment 1, wherein the liquid formulation has a pH of 3.5 to 4.0, preferably 3.6 to 3.8.

Exemplary Embodiment 3. The liquid formulation of embodiment 1 or embodiment 2, wherein the buffer system comprises a phosphate buffer, a citrate buffer, an acetate buffer, a histidine buffer, or a combination thereof.

Exemplary Embodiment 4. The liquid formulation of embodiment 1 or embodiment 2, wherein the buffer system comprises citric acid, sodium citrate, acetic acid, sodium acetate, or a combination thereof.

Exemplary Embodiment 5. The liquid formulation of embodiment 1 or embodiment 2, wherein the buffer system is a citrate buffer.

Exemplary Embodiment 6. The liquid formulation of embodiment 5, wherein the liquid formulation comprises from about 0.1 mg/mL to about 1.0 mg/mL of the citrate buffer.

Exemplary Embodiment 7. The liquid formulation of embodiment 1 or embodiment 2, wherein the liquid formulation comprises about 0.02% (w/v) of sodium citrate dihydrate and about 0.02% (w/v) of citric acid monohydrate.

Exemplary Embodiment 8. The liquid formulation of any one of embodiments 1-7, wherein the tonicity adjusting agent comprises sodium chloride, calcium chloride, magnesium chloride, or a combination thereof.

Exemplary Embodiment 9. The liquid formulation of any one of embodiments 1-7, wherein the tonicity adjusting agent comprises sodium chloride.

Exemplary Embodiment 10. The liquid formulation of embodiment 9, wherein the liquid formulation comprises about 9 mg/mL sodium chloride.

Exemplary Embodiment 11. The liquid formulation of any one of embodiments 1-10, wherein the liquid formulation has an osmolality of from about 285 mOsmol/kg to about 310 mOsmol/kg.

Exemplary Embodiment 12. The liquid formulation of any one of embodiments 1-11, wherein the liquid formulation comprises from about 0.05 mg/mL to about 1.0 mg/mL of hydromorphone hydrochloride.

Exemplary Embodiment 13. The liquid formulation of embodiment 12, wherein the liquid formulation comprises 0.2 mg/mL of hydromorphone hydrochloride.

Exemplary Embodiment 14. A ready-to-administer parenteral liquid formulation comprising: (a) 0.2 mg/mL of hydromorphone hydrochloride; (b) 9 mg/mL of sodium chloride; (c) 0.23 mg/mL of sodium citrate dihydrate; and (d) 0.22 mg/mL of citric acid monohydrate; wherein the liquid formulation has a pH of 3.5 to 4.2, wherein the liquid formulation has been terminally sterilized in a polymeric infusion container, and wherein the liquid formulation is stable for at least 6 months when stored at 25° C.±2° C. and not more than 40% RH.

Exemplary Embodiment 15. The liquid formulation of embodiment 14, wherein the liquid formulation has a pH of 3.6 to 3.8

Exemplary Embodiment 16. The liquid formulation of any one of embodiments 1-15, further comprising a pH adjusting agent.

Exemplary Embodiment 17. The liquid formulation of any one of embodiments 1-16, wherein the liquid formulation retains at least 95% w/w, preferably at least 98% w/w, of the hydromorphone hydrocholoride and has not more than 5% w/w, preferably not more than 2% w/w, of total related substances after storage at 25° C.±2° C. and not more than 40% RH for at least 6 months, preferably at least 12 months.

Exemplary Embodiment 18. A method of treating a patient in need of management of pain comprising parenterally administering to the patient the liquid formulation of any one of embodiments 1-17.

Exemplary Embodiment 19. The method of embodiment 18, wherein the pain is moderate to severe pain due to surgery, cancer, trauma (soft tissue and bone), biliary colic, myocardial infarction, burns, or renal colic.

Exemplary Embodiment 20. A polymeric infusion container filled with the liquid formulation of any one of embodiments 1-17.

Exemplary Embodiment 21. A method for manufacturing a ready-to-administer parenteral liquid formulation containing hydromorphone hydrochloride comprising: providing the liquid formulation containing hydromorphone hydrochloride in a polymeric infusion container, wherein the liquid formulation has an initial pH of 3.5 to 4.5; and terminally sterilizing the liquid formulation containing hydromorphone hydrochloride in the polymeric infusion container.

Exemplary Embodiment 22. The method of embodiment 21, wherein the liquid formulation has an initial pH of 3.5 to 4.0, preferably 3.6 to 3.8.

Exemplary Embodiment 23. The method of embodiment 21 or embodiment 22, wherein the liquid formulation further comprises a buffer system.

Exemplary Embodiment 24. The method of embodiment 23, wherein the buffer system is a citrate buffer.

Exemplary Embodiment 25. The method of embodiment 24, wherein the liquid formulation comprises from about 0.1 mg/mL to about 1.0 mg/mL of the citrate buffer.

Exemplary Embodiment 26. The method of embodiment 21, wherein the liquid formulation comprises about 0.02% (w/v) of sodium citrate dihydrate and about 0.02% (w/v) of citric acid monohydrate.

Exemplary Embodiment 27. The method of any one of embodiments 21-26, wherein the liquid formulation further comprises a tonicity adjusting agent.

Exemplary Embodiment 28. The method of embodiment 27, wherein the tonicity adjusting agent comprises sodium chloride.

Exemplary Embodiment 29. The method of any one of embodiments 21-26, wherein the liquid formulation comprises about 9 mg/mL sodium chloride.

J. EXAMPLES

In order to demonstrate the practice of the subject matter disclosed herein, the following examples have been prepared and tested. The examples should not, however, be viewed as limiting the scope of the invention.

Example 1: Dilution of Commercially Available Hydromorphone Hydrochloride

This study characterized the impact of terminal sterilization on a commercially available hydromorphone hydrochloride preparation diluted to 0.2 mg/mL.

Samples of Dilaudid® (Hydromorphone Hydrochloride) Injection (Fresenius Kabi USA, LLC) were diluted to 0.2 mg/mL using 0.9% Sodium Chloride Injection. The undiluted Dilaudid® (Hydromorphone Hydrochloride) Injection contained hydromorphone hydrochloride, 0.2% sodium citrate, 0.2% citric acid, and water for injection. The resulting diluted solution was filled into IV bags and subjected to terminal sterilization cycles in a Fedegari autoclave using an air overpressure cycle with target $F_0$ of 5, 10, 15, 20, 25 and 30 minutes. The resulting samples were analyzed for assay, impurities, pH, and osmolality.

The analytical results for these samples at time zero are listed in Table 3.

TABLE 3

Analytical Profile of Dilaudid Injection Diluted to 0.2 mg/mL in 0.9% Sodium Chloride Injection at Time Zero

| | | | Target $F_0$ (minutes) | | | | |
|---|---|---|---|---|---|---|---|
| | Control | 5 | 10 | 15 | 20 | 25 | 30 |
| pH | 4.18 | 4.02 | 4.17 | 4.31 | 4.33 | 4.23 | 4.30 |
| Assay (%) | 98.4 | 98.4 | 98.3 | 98.3 | 98.3 | 98.2 | 98.1 |
| Total Related Substances (%) | 0.09 | 0.14 | 0.19 | 0.20 | 0.23 | 0.24 | 0.31 |
| Osmolality (mOsm/kg) | 262 | 262 | 265 | 265 | 268 | 267 | 268 |

Bag samples were stored at 25° C. for three months and then tested for assay and related substances; the results of the three month samples are listed in Table 4.

TABLE 4

Analytical Profile of Dilaudid Injection Diluted to 0.2 mg/mL in 0.9% Sodium Chloride Injection after 3 months at 25° C.

| | | | Target $F_0$ (minutes) | | | | |
|---|---|---|---|---|---|---|---|
| | Control | 5 | 10 | 15 | 20 | 25 | 30 |
| Assay (%) | 100.3 | 99.9 | 99.5 | 99.9 | 100.3 | 99.7 | 99.8 |
| Total Related Substances (%) | 0.09 | 0.16 | 0.21 | 0.21 | 0.32 | 0.27 | 0.33 |

The data in Table 3 shows that the pH of the diluted hydromorphone hydrochloride is between 4.0 and 4.3 as a result of the citrate buffer system. The related substances were observed to increase with longer terminal sterilization cycles indicating that a shorter terminal sterilization cycle is preferred.

The assay and related substances following three months storage at 25° C. testing results in Table 4 indicate that under normal storage conditions, there are no significant changes in assay or related substances for each sample. The same trend was observed in related substances increasing with increased terminal sterilization time.

Example 2: Bulk Solution

This study characterized the impact of terminal sterilization on a 0.2 mg/mL bulk solution of hydromorphone hydrochloride. The drug product was prepared and analyzed to investigate the suitability of the formulation and container closure system.

The batch was prepared using the formulation in Table 5 according to the procedure described herein. Briefly, the process was performed under yellow lighting and involved the following steps: sparged water with nitrogen for 20 minutes; added 80% final volume of water to the vessel; added Sodium Chloride and mixed to dissolve; added Sodium Citrate Dihydrate and mixed to dissolve; added Citric Acid Monohydrate and mixed to dissolve; added Hydromorphone Hydrochloride (as a concentrate in water) and mixed to dissolve; checked pH and adjusted to 3.7 with Hydrochloric Acid; brought solution to q.s. with water; sparged solution with nitrogen for five minutes; and stored bulk solution under a nitrogen headspace until filling into bags.

TABLE 5

Formulation for Hydromorphone Hydrochloride in 0.9% Sodium Chloride Injection

| Ingredient | Function | Amount per mL |
|---|---|---|
| Hydromorphone Hydrochloride, USP | Active Ingredient | 0.2 mg |
| Sodium Chloride, USP | Tonicity | 9 mg |
| Sodium Citrate Dihydrate, USP | Buffering | 0.23 mg |
| Citric Acid Monohydrate, USP | Buffering | 0.22 mg |
| Sodium Hydroxide, NF | pH adjustment | pH adjustment |
| Hydrochloric Acid, NF | pH adjustment | pH adjustment |
| Water for Injection, USP | Aqueous Vehicle | q.s. ad 1 ml |

The bulk solution was filled (104 mL per bag) into PolyCine, single port IV bags and closed with a polypropylene twist-off.

The finished bags were then terminally sterilized in a Fedegari autoclave using an air overpressure cycle with a target $F_0$ of 15 minutes. The finished bags were then analyzed.

A sample filled into a type 1 glass vial with a fluoropolymer coated stopper was also terminally sterilized using the same cycle. A control sample not exposed to terminal sterilization stored in a glass vial was also tested. The density, viscosity and conductivity were measured using the bulk solution prepared for the stability study.

The results of the analysis are presented in Table 6 and Table 7.

TABLE 6

Analytical Profile of Prototype Hydromorphone
Hydrochloride in 0.9% Sodium Chloride Injection

|  | Control | TS Vial | TS Bag |
|---|---|---|---|
| Appearance | Clear, colorless solution free from signs of contamination | | |
| pH | 3.80 | Not Tested | 3.88 |
| Assay (%) | 100.3 | 100.7 | 100.5 |
| Total Related Substances (%) | <LOQ | 0.23 | 0.1 |
| Osmolality (mOsm/kg) |  |  | 286 |

TABLE 7

Viscosity, Conductivity and Density of Hydromorphone
Hydrochloride in 0.9% Sodium Chloride Injection

| Viscosity (cP) | 0.96 at 25° C. |
|---|---|
| Conductiviy (mS/cm) | 1584 at 25° C. |
| Density (g/mL) | 1.005 at 25° C. |

Currently available 0.2 mg/mL, 1 mg/mL, and 2 mg/mL formulations contain a 0.2% citrate buffer system. These results confirm that a 10 times reduction of buffer strength had no impact on the analytical profile of the diluted formulation after terminal sterilization.

A currently available 2 mg/mL formulation contains methylparaben and propylparaben as antimicrobial preservative agents used for multidose containers, such as vials. These results confirm that removing the preservatives had no impact on the analytical profile of the diluted formulation after terminal sterilization.

A currently available 2 mg/mL formulation also contains edetate disodium as a chelating agent. These results show that removing the edetate disodium resulted in an acceptable analytical profile of the diluted formulation after terminal sterilization.

There was no significant change in pH between the bulk solution stored in glass and bulk solution after terminal sterilization in an IV bag. Note that the target pH of Example 2 (3.8-3.9) was slightly lower than the observed pH of Example 1 (4.0-4.3).

There were no significant differences in appearance and assay for bulk solution terminally sterilized in glass compared to the same performed in the IV bag. The related substances were observed to be slightly higher for bulk solution terminally sterilized in glass compared to bulk terminally sterilized in the IV bag indicating that the IV bag may be more suitable for terminal sterilization of this formulation. The pH was not measured for bulk solution terminally sterilized in glass, but there was no significant change in pH between the bulk solution terminally sterilized in the IV bag and bulk solution not terminally sterilized and stored in glass.

There was a slight increase in related substances after terminal sterilization (increase of 0.10%), which was also observed for the commercially available preparation diluted in 0.9% Sodium Chloride Injection (increase of 0.11% for $F_0$ of 15 minutes). Furthermore, the total related substances observed were well within the established specification for the vial product of not more than 1.0%.

The results indicate that the disclosed formulations can withstand terminal sterilization cycles up to $F_0$ of 15 minutes. Longer cycles will result in higher levels of related substances, and therefore the terminal sterilization cycle time should be minimized.

Example 3: Stability Study

The effect of terminal sterilization on the stability of the product was characterized in three lots. Samples were prepared in accordance with Example 2 and filled into 100 mL IV bags for terminal sterilization. Bags were subsequently stored horizontally at 25° C. and 40% RH.

Samples were assessed by hydromorphone hydrochloride assay at 3, 6, 9, 12, 15, 18, and 24 months. pH and individual related substances were also assessed. Tables 8-10 show stability over time for each lot tested.

TABLE 8

| (lot A). | | | | | | | |
|---|---|---|---|---|---|---|---|
|  | 3 mo | 6 mo | 9 mo | 12 mo | 15 mo | 18 mo | 24 mo |
| hydromorphone HCl | 100.8 | 99.9 | 100.6 | 99.8 | 100.6 | 101.6 | 100.9 |
| pH | 3.8 | 3.7 | 3.8 | 3.7 | 3.8 | 3.7 | 3.7 |
| 2,2'-bishydromorphone | N.D. | <LOQ | <LOQ | <LOQ | <LOQ | <LOQ | <LOQ |
| dihydromorphine | N.D. | N.D. | N.D. | N.D. | N.D. | N.D. | N.D. |
| hydromorphone N-oxide | N.D. | N.D. | N.D. | N.D. | N.D. | N.D. | N.D. |
| bacterial endotoxin |  |  |  | <13 EU/ml | <13 EU/ml | <13 EU/ml | <13 EU/ml |
| fluid thioglycolate |  |  |  | sterile | sterile | sterile | sterile |
| tripticase soy broth |  |  |  | sterile | sterile | sterile | sterile |

LOQ = limit of quantitation;
N.D. = none detected

TABLE 9

(lot B).

| | 3 mo | 6 mo | 9 mo | 12 mo | 15 mo | 18 mo | 24 mo |
|---|---|---|---|---|---|---|---|
| hydromorphone HCl | 99.6 | 100.2 | 100.3 | 100.5 | 99.8 | 100.2 | 99.5 |
| pH | 3.8 | 3.7 | 3.7 | 3.8 | 3.8 | 3.7 | 3.9 |
| 2,2'-bishydromorphone | <LOQ | <LOQ | <LOQ | <LOQ | <LOQ | <LOQ | <LOQ |
| dihydromorphine | N.D. | <LOQ | N.D. | <LOQ | N.D. | <LOQ | N.D. |
| hydromorphone N-oxide | N.D. | N.D. | N.D. | N.D. | N.D. | N.D. | N.D. |
| bacterial endotoxin | | | | <13 EU/ml | <13 EU/ml | <13 EU/ml | <13 EU/ml |
| fluid thioglycolate | | | | sterile | sterile | sterile | sterile |
| tripticase soy broth | | | | sterile | sterile | sterile | sterile |

LOQ = limit of quantitation;
N.D. = none detected

TABLE 10

(lot C).

| | 3 mo | 6 mo | 9 mo | 12 mo | 15 mo | 18 mo | 24 mo |
|---|---|---|---|---|---|---|---|
| hydromorphone HCl | 99.2 | 100.0 | 99.6 | 100.0 | 99.4 | 100.1 | 100.1 |
| pH | 3.7 | 3.8 | 3.7 | 3.8 | 3.7 | 3.7 | 3.7 |
| 2,2'-bishydromorphone | <LOQ | <LOQ | <LOQ | <LOQ | <LOQ | <LOQ | <LOQ |
| dihydromorphine | N.D. | N.D. | N.D. | N.D. | N.D. | <LOQ | N.D. |
| hydromorphone N-oxide | N.D. | N.D. | N.D. | N.D. | N.D. | N.D. | N.D. |
| bacterial endotoxin | | | | <13 EU/ml | <13 EU/ml | <13 EU/ml | <13 EU/ml |
| fluid thioglycolate | | | | sterile | sterile | sterile | sterile |
| tripticase soy broth | | | | sterile | sterile | sterile | sterile |

LOQ = limit of quantitation;
N.D. = none detected

Example 4: Impact of pH

The effect of pH during the terminal sterilization process on the product was characterized in this study. Samples were prepared in accordance with Example 2 and filled into 100 mL IV bags for terminal sterilization, except that pH was varied as reported in the tables below. The pH of each formulation was adjusted using the listed pH adjusting agents from Table 1 as required to achieve the target pH. Filled bags were terminally sterilized with a target F0 of 11 minutes. Hydromorphone hydrochloride and individual related substances were assessed.

Table 11 shows hydromorphone hydrochloride and individual related substances for non-terminally sterilized samples and Table 12 shows hydromorphone hydrochloride and individual related substances for terminally sterilized samples.

TABLE 11

Non-terminally sterilized samples.

| | F1 | F2 | F3 | F4 | F5 | F6 |
|---|---|---|---|---|---|---|
| pH | 3.5 | 3.7 | 3.9 | 4.2 | 5.0 | 5.5 |
| hydromorphone HCl | 100.7 | 100.4 | 99.5 | 100.0 | 100.1 | 99.9 |
| Related Substances | | | | | | |
| Unknown RRT 0.57 | <LOQ | <LOQ | <LOQ | <LOQ | <LOQ | <LOQ |
| dihydromorphine | N.D. | N.D. | N.D. | N.D. | N.D. | N.D. |
| Unknown RRT 0.71 | <LOQ | N.D. | N.D. | N.D. | N.D. | N.D. |
| morphine sulfate | N.D. | N.D. | N.D. | N.D. | N.D. | N.D. |
| Unknown RRT 0.89 | N.D. | N.D. | N.D. | N.D. | N.D. | N.D. |
| hydromorphone N-oxide | N.D. | N.D. | N.D. | N.D. | N.D. | N.D. |
| Unknown RRT 1.46 | <LOQ | <LOQ | <LOQ | <LOQ | <LOQ | <LOQ |
| Placebo RRT 1.66 | N.D. | N.D. | N.D. | N.D. | N.D. | N.D. |
| Unknown RRT 1.76 | N.D. | N.D. | N.D. | N.D. | N.D. | N.D. |
| Unknown RRT 1.85 | <LOQ | <LOQ | <LOQ | <LOQ | <LOQ | <LOQ |
| Unknown RRT 1.98 | <LOQ | <LOQ | <LOQ | <LOQ | <LOQ | <LOQ |
| 2,2'-Bishydromorphone | <LOQ | <LOQ | <LOQ | <LOQ | <LOQ | <LOQ |
| Unknown RRT 2.05 | 0.09 | 0.09 | 0.09 | 0.09 | 0.09 | 0.09 |
| Unknown RRT 2.12 | LOQ | <LOQ | <LOQ | <LOQ | <LOQ | <LOQ |
| hydromorphone aldol dimer | N.D. | N.D. | N.D. | N.D. | N.D. | N.D. |
| Hydrocodone | N.D. | N.D. | N.D. | N.D. | N.D. | N.D. |

TABLE 11-continued

Non-terminally sterilized samples.

|  | F1 | F2 | F3 | F4 | F5 | F6 |
|---|---|---|---|---|---|---|
| Unknown RRT 2.27 | N.D. | N.D. | N.D. | N.D. | N.D. | N.D. |
| Unknown RRT 2.37 | <LOQ | <LOQ | <LOQ | <LOQ | <LOQ | <LOQ |
| Total | 0.09 | 0.09 | 0.09 | 0.09 | 0.09 | 0.09 |

TABLE 12

Terminally sterilized samples.

|  | F1 TS | F2 TS | F3 TS | F4 TS | F5 TS | F6 TS |
|---|---|---|---|---|---|---|
| pH | 3.5 | 3.7 | 4.0 | 4.2 | 5.0 | 5.5 |
| hydromorphone HCl | 100.7 | 100.6 | 99.6 | 100.4 | 100.1 | 99.5 |
| Related Substances |  |  |  |  |  |  |
| Unknown RRT 0.57 | <LOQ | <LOQ | <LOQ | <LOQ | <LOQ | 0.05 |
| dihydromorphine | <LOQ | <LOQ | <LOQ | <LOQ | 0.05 | 0.27 |
| Unknown RRT 0.71 | <LOQ | <LOQ | <LOQ | N.D. | <LOQ | <LOQ |
| morphine sulfate | N.D. | N.D. | N.D. | N.D. | N.D. | N.D. |
| Unknown RRT 0.89 | N.D. | N.D. | N.D. | N.D. | N.D. | <LOQ |
| hydromorphone N-oxide | N.D. | N.D. | N.D. | N.D. | N.D. | N.D. |
| Unknown RRT 1.46 | <LOQ | <LOQ | <LOQ | <LOQ | 0.06 | 0.14 |
| Placebo RRT 1.66 | <LOQ | <LOQ | <LOQ | <LOQ | <LOQ | <LOQ |
| Unknown RRT 1.76 | <LOQ | <LOQ | <LOQ | <LOQ | <LOQ | N.D. |
| Unknown RRT 1.85 | <LOQ | <LOQ | <LOQ | <LOQ | <LOQ | <LOQ |
| Unknown RRT 1.98 | <LOQ | <LOQ | N. D. | N.D. | N.D | N.D. |
| 2,2'-Bishydromorphone | <LOQ | <LOQ | <LOQ | <LOQ | <LOQ | N.D. |
| Unknown RRT 2.05 | 0.08 | 0.07 | 0.07 | 0.07 | <LOQ | N.D. |
| Unknown RRT 2.12 | <LOQ | <LOQ | <LOQ | <LOQ | <LOQ | <LOQ |
| hydromorphone aldol dimer | N.D. | N.D. | N.D. | N.D. | N.D. | N.D. |
| Hydrocodone | N.D. | N.D. | N.D. | N.D. | N.D | N.D. |
| Unknown RRT 2.27 | N.D. | N.D. | N.D. | N.D. | N.D. | <LOQ |
| Unknown RRT 2.37 | <LOQ | <LOQ | <LOQ | <LOQ | <LOQ | <LOQ |
| Total | 0.08 | 0.07 | 0.07 | 0.07 | 0.10 | 0.47 |

Samples F5 TS and F6 TS, which were terminally sterilized at pH of 5.0 and 5.5, respectively, contained higher amounts of dihydromorphine and/or higher amounts of total related substances as compared to non-terminally sterilized samples and samples terminally sterilized at pH ranging from 3.5 to 4.2. This further reinforces the observation that the product is more stable during the terminal sterilization process at relatively lower pH levels, even when using a shorter terminal sterilization cycle.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A ready-to-administer parenteral liquid formulation comprising:
   (a) 0.2 mg/mL of hydromorphone hydrochloride;
   (b) 9 mg/mL of sodium chloride;
   (c) 0.23 mg/mL of sodium citrate dihydrate; and
   (d) 0.22 mg/mL of citric acid monohydrate;
   wherein the liquid formulation has a pH of 3.5 to 4.2,
   wherein the liquid formulation has been terminally sterilized in a polymeric infusion container, wherein terminal sterilization is characterized by an $F_0$ value from 5 to 15, and
   wherein the liquid formulation is stable for at least 6 months when stored in the polymeric infusion container at 25° C.±2° C. and not more than 40% RH.

2. The liquid formulation of claim 1, wherein the liquid formulation has a pH of 3.6 to 3.8.

3. The liquid formulation of claim 1, further comprising a pH adjusting agent.

4. The liquid formulation of claim 1, wherein the liquid formulation retains at least 95% w/w of the hydromorphone hydrochloride and has not more than 5% w/w of hydromorphone degradation products after storage at 25° C.±2° C. and not more than 40% RH for at least 6 months.

5. The liquid formulation of claim 1, wherein the liquid formulation retains at least 98% w/w of the hydromorphone hydrocholoride and has not more than 2% w/w of hydromorphone degradation products after storage at 25° C.±2° C. and not more than 40% RH for at least 6 months.

6. A method of treating a patient in need of management of pain comprising parenterally administering to the patient the liquid formulation of claim 1.

7. A polymeric infusion container filled with the liquid formulation of claim 1.

8. The liquid formulation of claim 1, wherein the liquid formulation has been terminally sterilized by autoclave.

9. The liquid formulation of claim 1, wherein the polymeric infusion container is an intravenous infusion bag.

10. The liquid formulation of claim 9, wherein the intravenous infusion bag comprises one or more ports.

11. An intravenous infusion bag filled with at least 50 mL of the liquid formulation of claim 1.

12. An intravenous infusion bag filled with at least 50 mL of a ready-to-administer, sterile, parenteral liquid formulation, the ready-to-administer, sterile, parenteral liquid formulation comprising:
   (a) 0.2 mg/mL of hydromorphone hydrochloride;
   (b) 9 mg/mL of sodium chloride;
   (c) 0.23 mg/mL of sodium citrate dihydrate; and
   (d) 0.22 mg/mL of citric acid monohydrate;
   wherein the liquid formulation has a pH of 3.5 to 4.2,
   wherein the liquid formulation has an osmolality of from about 285 mOsmol/kg to about 310 mOsmol/kg,
   wherein the liquid formulation has been terminally sterilized in the intravenous infusion bag, wherein terminal sterilization is characterized by an $F_0$ value from 5 to 15, and
   wherein the liquid formulation is stable for at least 6 months when stored at 25° C.±2° C. and not more than 40% RH.

13. The liquid formulation of claim 1, wherein terminal sterilization is carried out at a temperature ranging from 115° C. to 130° C.

14. The intravenous infusion bag of claim 12, wherein the liquid formulation has a pH of 3.6 to 3.8.

15. The intravenous infusion bag of claim 12, wherein the liquid formulation has been terminally sterilized by autoclave.

16. The intravenous infusion bag of claim 12, wherein the intravenous infusion bag comprises one or more ports.

17. The intravenous infusion bag of claim 12, wherein terminal sterilization is carried out at a temperature ranging from 115° C. to 130° C.

18. The method of claim 6, wherein the pain is moderate to severe pain due to surgery, cancer, trauma (soft tissue and bone), biliary colic, myocardial infarction, burns, or renal colic.

* * * * *